(12) United States Patent
De Laat

(10) Patent No.: US 10,939,865 B2
(45) Date of Patent: Mar. 9, 2021

(54) VAGINAL DRUG DELIVERY DEVICE AND VAGINAL DIAGNOSTIC DEVICE

(71) Applicant: LiGalli B.V., The Hague (NL)

(72) Inventor: Wilhelmus Nicolaas Gerardus Maria De Laat, The Hague (NL)

(73) Assignee: LiGalli B.V., The Hague (NL)

( * ) Notice: Subject to any disclaimer, the term of this patent is extended or adjusted under 35 U.S.C. 154(b) by 16 days.

(21) Appl. No.: 15/764,258

(22) PCT Filed: Oct. 5, 2016

(86) PCT No.: PCT/EP2016/073788
§ 371 (c)(1),
(2) Date: Mar. 28, 2018

(87) PCT Pub. No.: WO2017/060299
PCT Pub. Date: Apr. 13, 2017

(65) Prior Publication Data
US 2018/0279941 A1     Oct. 4, 2018

(30) Foreign Application Priority Data

Oct. 6, 2015 (EP) ..................................... 15488465

(51) Int. Cl.
*A61B 5/00* (2006.01)
*A61M 31/00* (2006.01)
(Continued)

(52) U.S. Cl.
CPC .......... *A61B 5/4337* (2013.01); *A61B 5/4325* (2013.01); *A61B 5/6875* (2013.01);
(Continued)

(58) Field of Classification Search
CPC ... A61B 5/4337; A61B 5/6875; A61B 5/4325; A61B 10/0012; A61B 5/14546;
(Continued)

(56) References Cited

U.S. PATENT DOCUMENTS 5,928,195 A * 7/1999 Malamud .......... A61M 5/14593
604/141
2006/0084848 A1* 4/2006 Mitchnick .............. A61B 5/411
600/301
(Continued)

FOREIGN PATENT DOCUMENTS

CN         104334226 A      2/2015
WO    WO2011039680 A1     4/2011
(Continued)

*Primary Examiner* — Theodore J Stigell
*Assistant Examiner* — Rachel T. Smith
(74) *Attorney, Agent, or Firm* — Peter W. Schroen; Bret E. Field; Bozicevic, Field & Francis LLP

(57) ABSTRACT

The present invention is related to a vaginal drug delivery device and to a vaginal diagnostic device that comprises a first and second rigid member, wherein the first and/or second rigid member comprises a reservoir holding a medicament to be delivered, an opening, and a pump for pumping said medicament out of said opening, and/or wherein the first rigid member and/or second rigid member comprises a diagnostic device for performing an intravaginal diagnosis or measurement therefor. The device further comprises a first flexible member and flexible part, wherein at least one of the first flexible member and the flexible part is at least partially elastic having an elasticity such that the device can be squeezed from an extended shape to a collapsed shape. The device is pre-biased to assume the extended shape when little to no external force is being applied thereto. Furthermore, the device assumes a shape substantially corresponding to the extended shape when the device is inserted with the squeezed rigid member first, so that these naturally unfold in the formix posterior vaginae.

23 Claims, 5 Drawing Sheets

(51) Int. Cl.
*A61B 10/00* (2006.01)
*A61B 5/145* (2006.01)
*A61K 9/00* (2006.01)

(52) U.S. Cl.
CPC ....... *A61B 10/0012* (2013.01); *A61M 31/002* (2013.01); *A61B 5/002* (2013.01); *A61B 5/14532* (2013.01); *A61B 5/14546* (2013.01); *A61B 2560/0214* (2013.01); *A61K 9/0036* (2013.01); *A61M 2205/0216* (2013.01); *A61M 2205/3303* (2013.01); *A61M 2205/8206* (2013.01); *A61M 2210/1475* (2013.01); *A61M 2230/201* (2013.01)

(58) Field of Classification Search
CPC ................ A61B 5/14532; A61B 5/002; A61B 2560/0214; A61B 5/686; A61B 5/68; A61B 5/145; A61M 31/002; A61M 2205/8206; A61M 2210/1475; A61M 2205/0216; A61M 2205/3303; A61M 2230/201; A61M 2205/82; A61M 2205/33; A61K 9/0036
See application file for complete search history.

(56) References Cited

U.S. PATENT DOCUMENTS

| 2011/0039223 A1* | 2/2011 | Li .......................... B29C 35/02 433/6 |
| 2017/0106099 A1* | 4/2017 | Bellinger ............... A61K 47/10 |
| 2019/0008763 A1* | 1/2019 | Ulmann ................ A61K 31/573 |

FOREIGN PATENT DOCUMENTS

| WO | WO2012049676 A2 | 4/2012 |
| WO | WO2014135521 A1 | 9/2014 |

\* cited by examiner

VAGINAL DRUG DELIVERY DEVICE AND VAGINAL DIAGNOSTIC DEVICE

The present invention is related to a vaginal drug delivery device and to a vaginal diagnostic device. The present invention is also related to a combination of a vaginal drug delivery device and a vaginal diagnostic device.

Within the context of the present invention, a vaginal drug delivery device is a device configured for delivering drugs while inside the vagina. Similarly, a vaginal diagnostic device is configured for performing a diagnostic or measurement function while inside the vagina.

Vaginal drug delivery devices are known in the art. For instance, a low-dose contraceptive vaginal ring, known as Nuvaring®, is manufactured from poly(ethylene-co-vinyl acetate). This ring releases hormones to provide contraceptive protection.

This known ring is made from a flexible material allowing the ring to be squeezed to transform a shape of the ring for allowing the ring to be inserted into the vagina. The hormones are added to the flexible material in such a manner that the ring slowly releases the hormones after placement in the vagina.

A drawback of this known device is that the release of drugs is not entirely constant in time. Furthermore, the delivery rate of the drugs is continuous and has only one dosage. It is independent of variable factors such as age and weight. Obviously it cannot be switched off or on, other than being inserted or removed. It does not have the programmability (schedule) or adjustability (dose) possibility. A further drawback exists due to the fact that the drug delivery does not depend on ambient conditions and more in particular the physiological state of the user, e.g. whether the user is a fast/slow metabolizer, or the moment in the fertility cycle. Consequently, an inappropriate amount of drugs may be delivered.

An object of the invention is to provide a device with which the abovementioned disadvantages can be prevented or minimized.

According to the invention, this object is achieved with the vaginal drug delivery and/or diagnostic device as claimed in claim 1. This device comprises a first rigid member having a first and second end, a second rigid member having a third and fourth end, a first flexible member coupled between the first and third ends, and a flexible part coupled between the second and fourth ends. According to the present invention, the first rigid member and/or second rigid member comprises a reservoir holding a medicament to be delivered, an opening, and a pump for pumping the medicament out of said opening. Additionally or alternatively, the first rigid member and/or second rigid member comprises a diagnostic device for performing an intravaginal diagnosis or measurement therefore.

Furthermore, at least one of the first flexible member and the flexible part is at least partially elastic, wherein the elasticity of the at least one of the first flexible member and the flexible part is such that 1) the device can be squeezed to transform a shape of the device from an extended shape to a collapsed shape for allowing the device to be inserted into a vagina of a user, 2) the device is pre-biased to assume the extended shape when little to no external force is being applied thereto, said extended shape corresponding to a substantially oval or annular ring shape, and 3) the device assumes a shape substantially corresponding to the extended shape when the device is inserted into the vagina with the squeezed rigid parts first. The rigid parts will assume a natural position in the deepest part of the vagina, the fornix posterior vaginae.

The invention proposes to divide the vaginal drug delivery and/or diagnostic device into rigid and flexible components, wherein the functional parts of the drug delivery and/or diagnostic mechanism, which are mostly sensitive and/or rigid components, are incorporated in the rigid component(s) and wherein the flexible components allow the device to be squeezed to transform the shape of the device to allow a user to place the device inside the vagina. Here, it is noted that the elasticity of the device, originating from at least one of the first flexible member and the flexible part, causes the device to substantially return to its original shape. This shape is important as the device should not or hardly be felt by the user when placed inside the vagina. Furthermore, the shape should be such that it should not or hardly be noticeable during coitus. It is therefore preferable when an outer surface of the device is substantiality smooth. In addition, a smooth outer surface prevents or limits irritation of the vaginal wall.

In an embodiment, the at least one of the first flexible member and the flexible part is at least partially made from an elastic material.

In an embodiment, the first flexible member acts as a hinge to allow the first and second rigid members to move with respect to each other. In this embodiment, the first flexible member is made of an elastic and flexible material, whereas the flexible part is merely flexible having little to no elasticity. Hence, in this embodiment, the first and second rigid members can be moved to each other by applying an external force. At the same time, the flexible part flexes to accommodate this movement. Once the external force is removed, the device springs back to its original form due to the elasticity of the first flexible member.

The flexible part could comprise a second flexible member, a third flexible member, a fourth flexible member, a third rigid member having a fifth and sixth end, and a fourth rigid member having a seventh and eighth end. Here, the second flexible member is coupled in between the second end and the fifth end, the third flexible member is coupled in between the fourth end and the seventh end, and the fourth flexible member is coupled in between the sixth end and the eighth end.

In an alternative embodiment, the flexible part is at least partially elastic. For example, at least one of the second, third, and fourth flexible member is at least partially made from an elastic material. Hence, in this embodiment the flexible part could also provide a pre-bias to assume the extended shape.

Furthermore, the second, third, or fourth rigid member may comprise a source of electrical energy, such as a battery, for providing electrical energy to the pump and/or diagnostic device. The device may further comprise a first flexible electrical connection in between the energy source and the pump and/or diagnostic device. This first flexible electrical connection can be accommodated in the flexible member(s) arranged in between the pump and/or diagnostic device and the rigid member that holds the electrical energy source.

The pump and the energy source can be accommodated in different rigid members among the first, second, third, and fourth rigid members, and/or the diagnostic device and the energy source can be accommodated in different rigid members among the first, second, third, and fourth rigid members.

As stated before, functional parts of the drug delivery or diagnostic mechanism can be accommodated in the rigid components of the device. For example, the first, second, third, or fourth rigid member may comprise a controller for controlling the pump and/or diagnostic device. Additionally or alternatively, the first, second, third, or fourth rigid member may comprise a sensor for measuring biochemical compounds and/or medicines, such as a hormone levels like oestradiol, Luteinizing hormone (LH), and progesterone or glucose. The sensor can also be used to measure other biochemical parameters and/or medication levels. Additionally or alternatively, the first, second, third, or fourth rigid member may comprise such sensor, wherein the controller is configured for controlling the pump in dependence of a measurement performed by this sensor. The measurement can be done physicochemically, or as assay, in the cervical mucus or transudate of the vaginal wall.

The device may further comprise a second flexible electrical connection in between the sensor and the controller, and/or a third flexible electrical connection in between the energy source and the controller, and/or a fourth flexible electrical connection in between the controller and the pump and/or diagnostic device, wherein the second, third, and/or fourth flexible electrical connection is at least partly accommodated in the first, second, third, and/or fourth flexible member.

The first, second, third, and/or fourth rigid member and the first, second, third, and/or fourth flexible member can be formed, preferably by injection moulding, using a respective material composition, and wherein the material composition(s) used for the rigid members differs from the material composition(s) used for the flexible members. Here, the couplings between the flexible and rigid members can be fixed, preferably formed during the injection moulding of the flexible and/or rigid members.

The material composition used for at least one of the rigid members comprises one or more of the materials of the group consisting of: polyolefin, ABS (acrylonitrile butadiene styrene), PA (polyamide), PBT copolyesters (polybutylene terephthalate), polyethylene, polypropylene, polystyrene, polyester, polyester (PLA and other biosorbable plastics), polycarbonate, polyvinyl chloride, polyethersulfone, polysulfone, and polyetheretherketone.

The material composition used for at least one of the flexible members may comprise one or more of the materials of the group consisting of: LSR (liquid silicone rubber), thermoplastic elastomers (TPE, thermoplastic polyurethane (TPU), thermoset elastomers such as silicone rubber, butadiene rubber, fluoropolymers, poly(p-xylylene) (parylene), and polyacrylate such as poly(methyl methacrylate) (PMMA).

To allow a user to easily place the device inside the vagina, it is advantageous if the device in the extended shape extends around a central axial axis, wherein an outer diameter of the device, determined in a plane perpendicular to the axial axis, lies in a range between 50 and 70 mm, and more preferably between 55 and 65 mm, and wherein an inner diameter of the device, determined in a cross section parallel to the axial axis, lies in a range between 4 and 8 mm.

In an embodiment, the device has a ring shape with a substantially constant outer diameter. Moreover, an internal diameter of the device, determined in a plane perpendicular to the axial axis, can be smaller near at least one of the rigid members. The part of the device containing functional parts of the drug delivery or diagnostic mechanism, such as the medicament container or pump, will naturally reside in the deeper part of the vagina, close to the cervix uteri.

At least one of the rigid members in isolation may have a bending strength such that when a force of 0.5N is applied at a force application point that is at a distance of 20 mm relative to a fixation point at which the rigid member is held fixed, a bending angle, which corresponds to a rotation angle related to a rotation about the fixation point of a line that extends between the fixation point and the force application point due to the application of the force, does not exceed 10 degrees.

At least one of the flexible members in isolation may have a bending strength such that when a force of 0.5N is applied at a force application point that is at a distance of 20 mm relative to a fixation point at which the rigid member is held fixed, a bending angle, which corresponds to a rotation angle related to a rotation about the fixation point of a line that extends between the fixation point and the force application point due to the application of said force, exceeds 30 degrees.

The vaginal drug delivery and/or diagnostic device may further comprise a transmitter configured for wireless transmission of measurement data corresponding to measurements performed by the sensor and/or measurement data or diagnosis information outputted by the diagnostic device. Additionally or alternatively, the device may comprise a receiver for wirelessly receiving control commands for remote control of at least one of the pump, the sensor, and the diagnostic device. The receiver and transmitter may be combined into a single transceiver unit.

Next, the invention will be described in more detail referring to the appended figures, wherein:

FIG. 1 schematically illustrates an embodiment of a device in accordance with the present invention;

Figure 1:
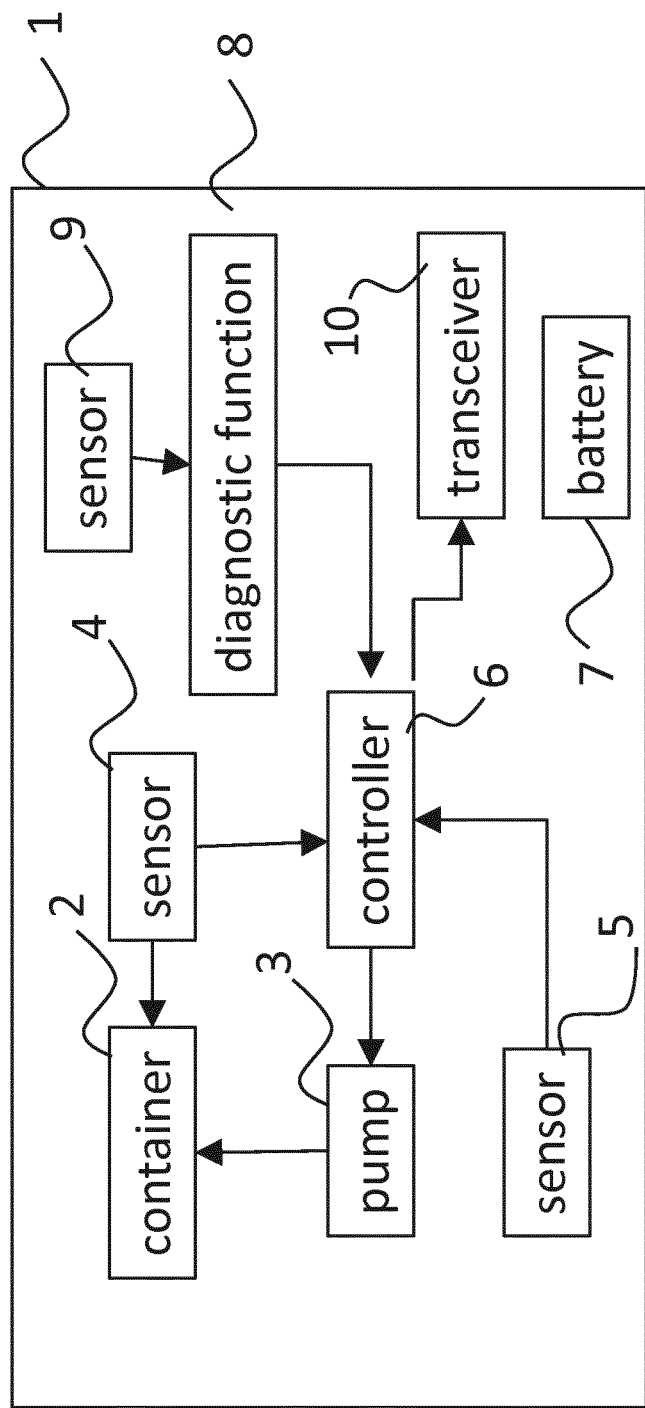

FIG. 1 schematically illustrates an embodiment of a device 1 in accordance with the present invention. This device comprises a container 2 for holding a medicament. A pump 3 is used for pumping the medicament out of the opening. A sensor 4 is used to determine the flow rate of medicament through the opening. The flow sensor may act indirectly by measuring the filling level of container 2.

Device 1 comprises a further sensor 5 that measures for example a hormone level or glucose, or a medicine. Information from sensor 4 and from sensor 5 is fed to a controller 6 which controls pump 3. Hence, it is possible to deliver drugs inside the vagina based on hormone levels measured inside the vagina and/or the level inside container 2.

Device 1 could be embodied as a device for delivering GnRH for ovulation induction of the Kallmann syndrome (or of other hypo-hypo conditions). In this case, sensor 5 could be configured for measuring oestradiol and/or LH (in the cervical mucus or transudate of the vaginal mucosa) for prediction of the pending ovulation and discontinuation of the drug delivery. Device 1 could also be embodied as a device for delivering insulin. In this case, sensor 5 could be configured for measuring the glucose level (in the transudate of the vaginal mucosa) allowing controller 6 to subsequently change the dose of insulin. Sensor 5 could also be embodied as a sensor that measures a level of medicine in the body via transudate of the mucosa. This information could be used by controller 6 to subsequently change the vaginal drug delivery if needed. Especially in known non-compliant patients (e.g. depression and other chronic diseases) a constant and therapeutic level of medication is of vital importance.

A battery 7 is used to provide electrical power to any of the components in device 1 that require electrical power. It should be appreciated that other forms of energy could equally be used.

Device 1 may further comprise a diagnostic function 8 that is coupled to a sensor 9, in which the sensor measures a hormone level, a physiological parameter, or medicine. This diagnostic function could be used for ovulation prediction, or monitoring of an assisted reproduction cycle (IVF, ovulation stimulation, artificial insemination) where monitoring the (increase of the) hormone levels like E2, LH and progesterone to diagnose the pending ovulation or moment of ovulation induction (with HCG) is of vital importance. Alternatively, device 1 could be measuring the glucose level (in the transudate of the vaginal mucosa) to determine the need for insulin delivery for diabetes treatment. Here, diagnostic function 8 can be embodied as a processor and may be integrated with controller 6. Based on measurements obtained by sensor 9, diagnostic function 8 performs a diagnosis or solely processes the measurements. This information is fed back to controller 6, which may control pump 3 depending on the output of diagnostic function 8. Alternatively or additionally, controller 6 supplies data from sensor 4, sensor 5, and/or diagnostic function 8 to a transceiver 10 for wirelessly transmitting the data to a receiver preferably external to the body of the user. Moreover, device 1 may be limited to performing the measurements and/or making the diagnosis. For instance, device 1 may be configured to only measure the glucose level and to transmit the corresponding measurement data to an external device. This external device may display the measurement data and/or may comprise or control an insulin pump. This approach can be extended to other types of measurements as well.

In general, transceiver 10 allows device 1 to communicate results to an outside computer or handheld device. This data transfer may be related to the drug delivery function only (dosage, frequency, timing), thus indicating the rate of compliance to therapy, or to the diagnostic function only (prediction of moment of ovulation, measurement of glucose level or level of medication), or to the integrated functions of both. Additionally or alternatively, transceiver 10 may also be used to receive data from an external transmitter to control the functionality of device 1. Such data could for instance comprise control data that instructs controller 6 to start/stop delivering the medicament using pump 3 or to start/stop performing a diagnosis by diagnostic function 8.

It should be apparent that not every function or component is required. For instance, diagnostic function 8 and sensor 9 could be omitted if such functionality is not required or desired. Moreover, transceiver 10 could be embodied as a transmitter or receiver only.

Figure 2:
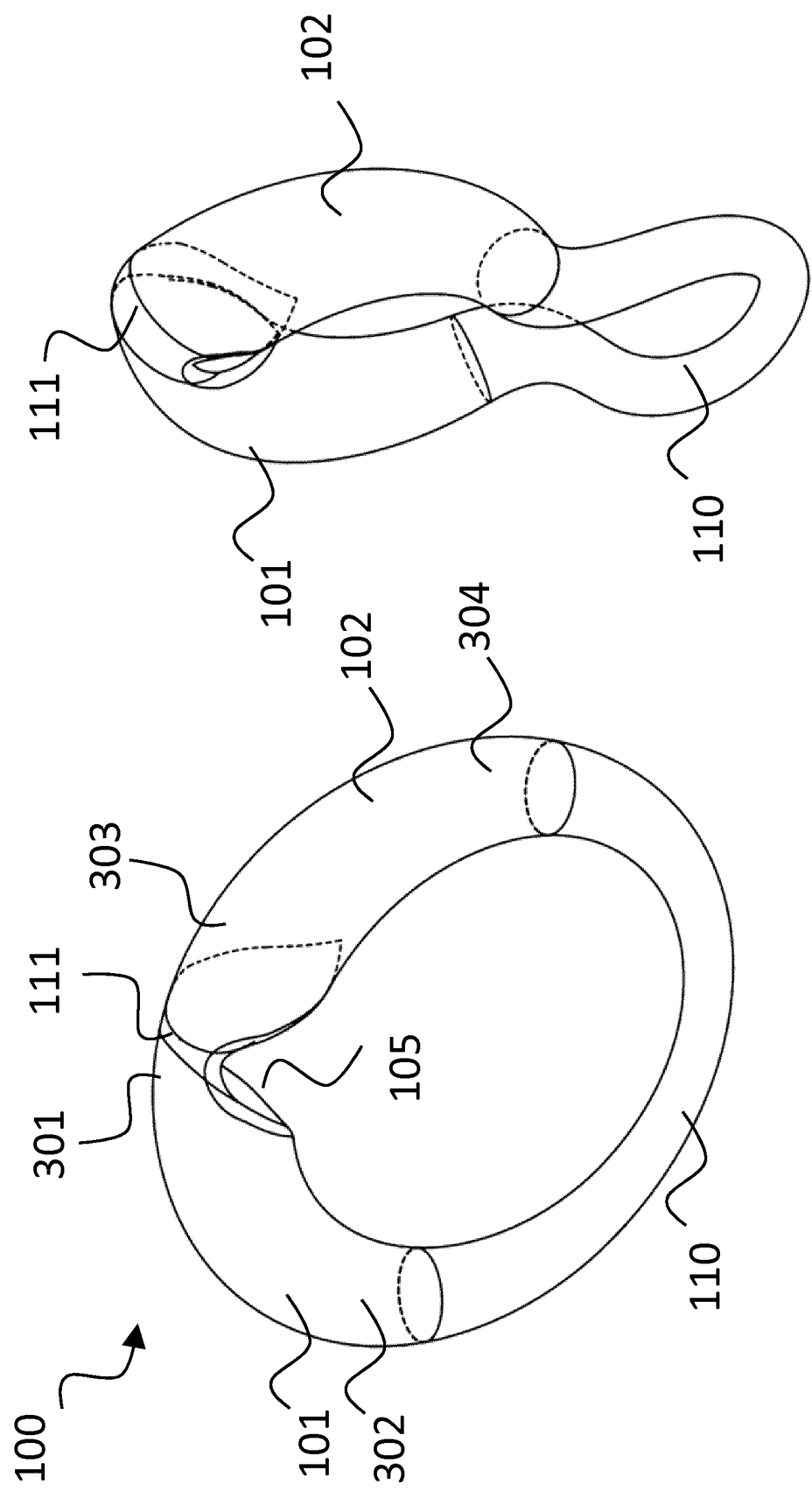
FIG. 2 illustrates a possible shape of a device in accordance with the present invention in an extended and collapsed state.

FIG. 2 illustrates a possible shape of a device in accordance with the present invention in an extended (left) and collapsed state (right). This shape comprises a first rigid member 101, a second rigid member 102, a first flexible member 111, and a flexible part 110. The first rigid member 101 has a first end 301 and a second end 302. The second rigid member 102 also has a first end 303 and a second end 304. Here, first flexible member 111 is made of an elastic material and comprises a recess 105 to allow first and second rigid member 101, 102 to move towards each other when device 100 is squeezed into the collapsed state.

According to the invention, the functional parts of the drug delivery and/or diagnostic mechanism are incorporated into the rigid members 101, 102, whereas the (electrical) interconnect can be accommodated in the flexible member 111 or flexible part 110.

Figure 3:
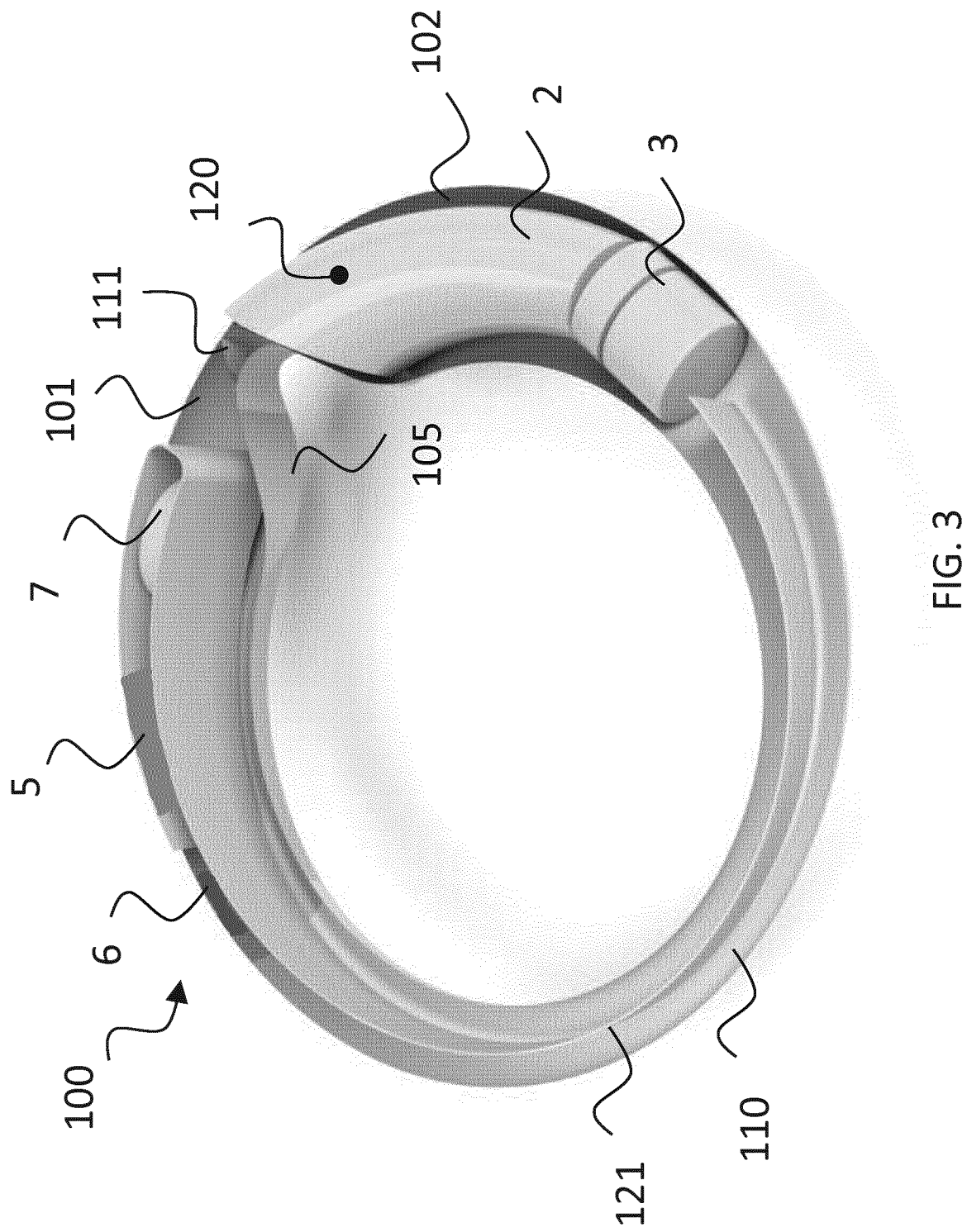
FIG. 3 illustrates the device of FIG. 2 showing a possible location of some of the components of the device of FIG. 1.

FIG. 3 illustrates the device of FIG. 2 showing an exemplary arrangement of some of the components of the device of FIG. 1. Here, it can be seen that the functional parts of the drug delivery mechanism, i.e. battery 7, controller 6, pump 3, reservoir 2, and sensor 5 are incorporated in first rigid member 101 and second rigid member 102. Moreover, an opening 120 can be identified through which the medicament held in reservoir 2 is pumped out by pump 3. This opening will be located at such a place on the outer perimeter of the ring to guarantee optimal contact with the vaginal mucosa. Furthermore, an electrical interconnect 121 can be seen that connects the various components to each other and to battery 7.

In FIG. 3, a transceiver may be incorporated in controller 6 or may alternatively be arranged as a separate component in first rigid member 101. This transceiver allows data communication between controller 6 and external systems or devices for remote control or for exchanging data such as measurement data.

First rigid member 101 may be provided with an opening or membrane to enable sensor 5 to perform a predefined measurement. Similar openings or membranes can be provided if additional sensors are used which may or may not be arranged in first rigid member 101. These openings will be located at such places on the outer or inner perimeter of the ring to guarantee optimal contact with the vaginal mucosa or cervical mucus.

A possible manner to fabricate the device shown in FIG. 3 is described next. First, the relevant components of the drug delivery mechanism are arranged inside a mold. To this end, these components can be arranged in one or more rigid shells to protect these components from the remaining processing steps. Furthermore, the electrical interconnect, which preferably is flexible, is also arranged inside the mold. More in particular, all the components are electrically connected at this point. Thereafter the mold is closed, and a suitable material or materials is injection molded. In this manner, flexible part 110 and flexible member 111 are formed and surround the electrical interconnect. This same material ensures that the various shells, if used, become fixedly connected to flexible part 110 and flexible member 111. Hence, in this fabrication process, a rigid member may comprise a rigid shell that is generally coated or covered with the material that is used for flexible member 111 and/or flexible part 110. Alternatively, flexible member 111 can be made from a different material. For instance, flexible member 111 is made from elastic material whereas flexible part 110, and therefore the material that may cover the shells of rigid members 101, 102, is merely flexible. Such material for flexible member 111 can be placed inside the mold prior to injection molding.

It should be noted that the various components for the drug delivery and diagnosis mechanism need not be fully arranged inside the rigid members. In some cases, the components may extend into the flexible and/or elastic members or parts of the device.

Figure 4:
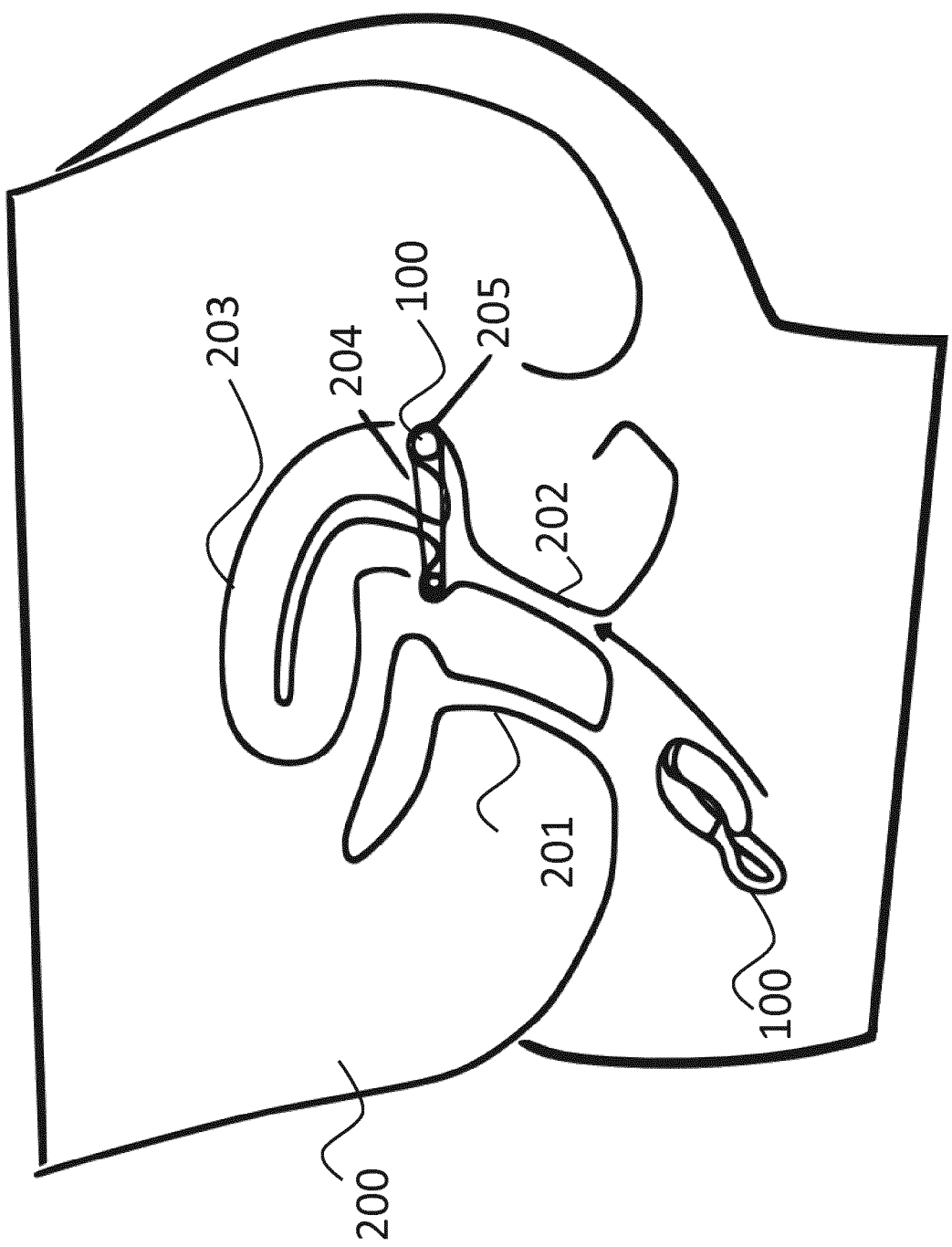
FIG. 4 illustrates the device of FIG. 3 being inserted into the vagina.

FIG. 4 illustrates the device of FIG. 3 being inserted into the vagina. Here, a body 200 of the user is shown indicating the urethra 201, the vagina 202, and the uterus 203. Prior to inserting device 100, it is squeezed to transform the shape into the collapsed state. Thereafter, the user inserts device 100 with the squeezed rigid parts first into vagina 202, and moves device 100 close to cervix uteri 204 or fornix posterior vaginae 205, where device 100 is released. Due to its elasticity, device 100 regains its original shape, at least to a substantial extent. Due to its shape and size, device 100 rests against the vaginal wall. This positioning allows appropriate measurements to be performed. Moreover, this position ensures that little to no irritation or pain is observed by the user and that any impact of device 100 on coitus is minimized.

Figure 5:
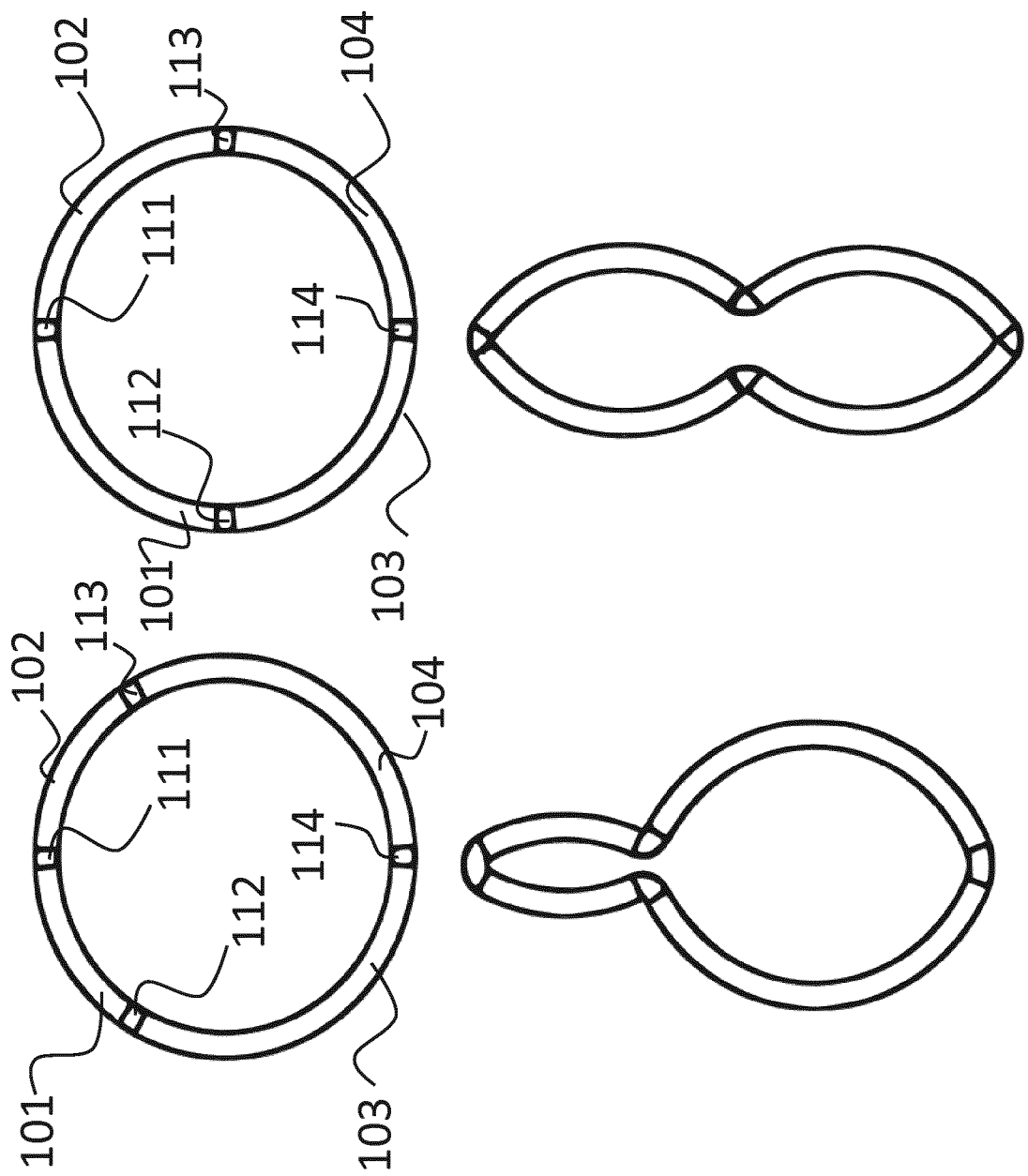
FIG. 5 illustrates different possible shapes of a device in accordance with the present invention in an extended and collapsed state.

FIG. 5 illustrates different possible shapes of a device in accordance with the present invention in an extended and collapsed state. Comparing these shapes to the shape indicated in FIG. 2 it can be observed that flexible part 110 has been replaced by a second flexible member 112, a third flexible member 113, a fourth flexible member 114, a third rigid member 103, and a fourth rigid member 104.

In FIG. 5, the shapes in the top half indicate the extended shapes, whereas the shapes in the bottom half represent the corresponding collapsed states. The shape to be used depends on the amount of functional parts to be accommodated in the rigid members and the relative sizes of these components.

In the above, the invention has been disclosed by referring to embodiments thereof. It should be appreciated by the person skilled in the art that various modifications are possible without deviating from the invention, the scope of which is defined by the appended claims.

The invention claimed is:

1. A vaginal drug delivery and/or diagnostic device, comprising:
 a first rigid member having a first and second end;
 a second rigid member having a third and fourth end;
 a first flexible member coupled between the first and third ends; and
 a flexible part coupled between the second and fourth ends;
 wherein the first rigid member and/or second rigid member comprises:
 a reservoir holding a medicament to be delivered, an opening, and a pump for pumping said medicament out of said opening; and/or
 a diagnostic mechanism for performing an intravaginal diagnosis or measurement therefor;
 wherein the first rigid member, the second rigid member and the flexible part define a plane;
 wherein at least one of the first flexible member and the flexible part is at least partially elastic; and
 wherein the elasticity of the at least one of the first flexible member and the flexible part is such that:
 the vaginal drug delivery and/or diagnostic device is configured to be squeezed to transform a shape of the vaginal drug delivery and/or diagnostic device from an extended shape to a collapsed shape for allowing the device to be inserted into a vagina of a user, wherein in the collapsed shape the first rigid member, the second rigid member and the flexible part are substantially squeezed together in their plane;
 the vaginal drug delivery and/or diagnostic device is pre-biased to assume the extended shape when little to no external force is being applied thereto, said extended shape corresponding to a substantially oval or annular ring shape; and
 the vaginal drug delivery and/or diagnostic device assumes a shape substantially corresponding to the extended shape when the device is placed and released at or near a fornix posterior vaginae of a user.

2. The vaginal drug delivery and/or diagnostic device according to claim 1, wherein an outer surface of the vaginal drug delivery and/or diagnostic device is substantially smooth.

3. The vaginal drug delivery and/or diagnostic device according to claim 1, wherein said at least one of the first flexible member and the flexible part is at least partially made from an elastic material.

4. The vaginal drug delivery and/or diagnostic device according to claim 1, wherein the flexible part comprises:
 a second flexible member;
 a third flexible member;
 a fourth flexible member;
 a third rigid member having a fifth and sixth end; and
 a fourth rigid member having a seventh and eighth end;
 wherein the second flexible member is coupled in between the second end and the fifth end;
 wherein the third flexible member is coupled in between the fourth end and the seventh end; and
 wherein the fourth flexible member is coupled in between the sixth end and the eighth end.

5. The vaginal drug delivery and/or diagnostic device according to claim 4, wherein the second, third, or fourth rigid member comprises a source of electrical energy for providing electrical energy to said pump and/or diagnostic mechanism, said vaginal drug delivery and/or diagnostic device further comprising a first flexible electrical connection in between said source of electrical energy and said pump and/or diagnostic mechanism, said first flexible electrical connection being accommodated in the flexible member(s) arranged in between the pump and/or diagnostic mechanism and the second, third or fourth rigid member that holds the electrical energy source.

6. The vaginal drug delivery and/or diagnostic device according to claim 5, wherein the pump and the source of electrical energy are accommodated in different rigid members among the first, second, third, and fourth rigid members; and/or
 wherein the diagnostic mechanism and the source of electrical energy are accommodated in different rigid members among the first, second, third, and fourth rigid members.

7. The vaginal drug delivery and/or diagnostic device according to claim 4, wherein the first, second, third, or fourth rigid member comprises a controller for controlling said pump and/or diagnostic mechanism.

8. The vaginal drug delivery and/or diagnostic device according to claim 7, wherein:
 the diagnostic mechanism comprises a sensor for measuring biochemical compounds and/or medicines, and/or
 the first, second, third, or fourth rigid member comprising the sensor, said controller being configured for controlling said pump depending on a measurement performed by said sensor.

9. The vaginal drug delivery and/or diagnostic device according to claim 8, said vaginal drug delivery and/or diagnostic device further comprising a second flexible electrical connection in between said sensor and said controller, and/or a third flexible electrical connection in between said source of electrical energy and said controller, and/or a fourth flexible electrical connection in between said controller and said pump and/or diagnostic mechanism, wherein said second, third, and/or fourth flexible electrical connection is at least partly accommodated in the first, second, third, and/or fourth flexible member.

10. The vaginal drug delivery and/or diagnostic device according to claim 8, further comprising a transmitter configured for wireless transmission of measurement data corresponding to measurements performed by the sensor and/or diagnosis information outputted by the diagnostic mechanism.

11. The vaginal drug delivery and/or diagnostic device according to claim 10, further comprising a receiver for wirelessly receiving control commands for remote control of at least one of the pump, the sensor, and the diagnostic mechanism, wherein the receiver and transmitter may be combined into a single transceiver unit.

12. The vaginal drug delivery and/or diagnostic device according to claim 8, wherein the biochemical compounds and/or medicines are hormone levels like oestradiol, luteinizing hormone (LH), and progesterone or glucose, and/or other biochemical parameters and/or medication levels.

13. The vaginal drug delivery and/or diagnostic device according to claim 4, wherein the first, second, third, and/or fourth rigid member and the first, second, third, and/or fourth flexible member is formed using a respective material composition, and wherein the material composition(s) used for the rigid members differs from the material composition (s) used for the flexible members;
wherein couplings between the flexible and rigid members are fixed; and/or
wherein the material composition used for at least one of the rigid members comprises one or more of the materials of the group consisting of: polyolefin, ABS (acrylonitrile butadiene styrene), PA (polyamide), PBT copolyesters (polybutylene terephthalate), polyethylene, polypropylene, polystyrene, polyester (PLA and other biosorbable plastics), polycarbonate, polyvinyl chloride, polyethersulfone, polysulfone, and polyetheretherketone.

14. The vaginal drug delivery and/or diagnostic device according to claim 13, wherein the first, second, third, and/or fourth rigid member and the first, second, third, and/or fourth flexible member is formed by injection moulding.

15. The vaginal drug delivery and/or diagnostic device according to claim 13, wherein the couplings between the first flexible member and the first and second rigid members are formed during injection moulding of the first flexible member and/or the first and second rigid members.

16. The vaginal drug delivery and/or diagnostic device according to claim 13, wherein the material composition used for at least one of the flexible members comprises one or more of the materials of the group consisting of: LSR (liquid silicone rubber), thermoplastic elastomers (TPE, thermoplastic polyurethane (TPU)), and thermoset elastomers.

17. The vaginal drug delivery and/or diagnostic device according to claim 16, wherein the thermoset elastomers are silicone rubber, butadiene rubber, fluoropolymers, poly(p-xylylene) (parylene), and .

18. The vaginal drug delivery and/or diagnostic device according to claim 17, wherein the polyacrylate is poly (methyl methacrylate) (PMMA).

19. The vaginal drug delivery and/or diagnostic device according to claim 4, wherein at least one of the rigid members in isolation has a bending strength such that when a force of 0.5 N is applied at a force application point that is at a distance of 20 mm relative to a fixation point at which at least one of the rigid members is held fixed, a bending angle, which corresponds to angle of rotation related to a rotation about the fixation point of a line that extends between the fixation point and the force application point due to the application of said force, does not exceed 10 degrees.

20. The vaginal drug delivery and/or diagnostic device according to claim 1, said vaginal drug delivery and/or diagnostic device in the extended shape extending around a central axial axis;
wherein an outer diameter of the vaginal drug delivery and/or diagnostic device, determined in a plane perpendicular to said axial axis, lies in a range between 50 and 70 mm; and
wherein an inner diameter of the vaginal drug delivery and/or diagnostic device, determined in a cross section parallel to the axial axis, lies in a range between 4 and 8 mm.

21. The vaginal drug delivery and/or diagnostic device according to claim 20, wherein the outer diameter of the vaginal drug delivery and/or diagnostic device, determined in the plane perpendicular to said axial axis, lies in a range between 55 and 65 mm.

22. The vaginal drug delivery and/or diagnostic device according to claim 20, wherein the vaginal drug delivery and/or diagnostic device has a ring shape with a substantially constant outer diameter and/or wherein an internal diameter of the vaginal drug delivery and/or diagnostic device, determined in a plane perpendicular to said axial axis, is smaller near at least one of the rigid members.

23. The vaginal drug delivery and/or diagnostic device according to claim 1, wherein at least one of the flexible members in isolation has a bending strength such that when a force of 0.5 N is applied at a force application point that is at a distance of 20 mm relative to a fixation point at which at least one of the rigid members is held fixed, a bending angle, which corresponds to a rotation angle related to a rotation about the fixation point of a line that extends between the fixation point and the force application point due to the application of said force, exceeds 30 degrees.

* * * * *

UNITED STATES PATENT AND TRADEMARK OFFICE
CERTIFICATE OF CORRECTION

PATENT NO. : 10,939,865 B2
APPLICATION NO. : 15/764258
DATED : March 9, 2021
INVENTOR(S) : Wilhelmus Nicolaas Gerardus Maria De Laat Page 1 of 1

It is certified that error appears in the above-identified patent and that said Letters Patent is hereby corrected as shown below:

In the Claims

Please replace "and ." in Claim 17 with -- and polyacrylate. -- (Column 10, Line 4).

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*